United States Patent [19]
Rowe et al.

[11] Patent Number: 5,830,165
[45] Date of Patent: Nov. 3, 1998

[54] UPPER EXTREMITY SWATHE SLING APPARATUS

[76] Inventors: Denis O. Rowe, 136 Boxwood Dr., Franklin, Tenn. 37064; John Hutson, 877 Hillhaven Ct., Nashville, Tenn. 37220; Buddy Taylor, 2713 Reynolds Forest Ct., Winston-Salem, N.C. 27107

[21] Appl. No.: 546,622

[22] Filed: Oct. 23, 1995

Related U.S. Application Data

[63] Continuation of Ser. No. 176,719, Jan. 3, 1994, abandoned.

[51] Int. Cl.[6] .................................................... A61F 5/00
[52] U.S. Cl. .................................. 602/4; 602/5; 602/20; 602/21; 128/876; 128/878
[58] Field of Search .............................. 602/4, 5, 20, 62, 602/64; 128/877–880, 874; 2/44, 45

[56] References Cited

U.S. PATENT DOCUMENTS

| | | | |
|---|---|---|---|
| 2,460,589 | 1/1949 | Lewis | 602/4 |
| 3,307,538 | 3/1967 | Groll | 602/4 |
| 3,888,244 | 6/1975 | Lebold | 602/4 |
| 4,285,337 | 8/1981 | Cosentino | 128/133 |
| 4,372,301 | 2/1983 | Hubbard et al. | 602/4 |
| 4,526,164 | 7/1985 | Bihl | 602/4 |
| 4,716,895 | 1/1988 | Marques et al. | 128/94 |
| 4,836,195 | 6/1989 | Berrehail | 602/20 |
| 4,878,490 | 11/1989 | Scott | 128/77 |
| 4,895,142 | 1/1990 | Liptak | 602/4 |
| 4,896,660 | 1/1990 | Scott | 602/20 |
| 5,141,488 | 8/1992 | Schrader | 602/4 |
| 5,358,470 | 10/1994 | Johnson | 602/4 |

Primary Examiner—Richard J. Apley
Assistant Examiner—Kim L. Lee

[57] ABSTRACT

The present invention is a sling-like swathe of flexible material capable of being wrapped around the body of the wearer. The invention includes a first looped end opposite a free end. The looped end accommodates an appendage such as an arm, wrist, hand or the like and the remaining length of the invention is configured to enable the wearer to wrap the invention around his body and effectively immobilize the appendage placed in the looped end by constraining the movement of the appendage against the body of the wearer. The preferred material of the present invention is a tricot-backed, brushed nylon laminate and incorporates hook and loop material spaced at various locations to enable cooperating fixation with a side of the flexible material.

20 Claims, 2 Drawing Sheets

UPPER EXTREMITY SWATHE SLING APPARATUS

This is a continuation of application Ser. No. 08/176,719 filed on Jan. 3, 1994, now abandoned.

BACKGROUND OF THE INVENTION

1. Field of the Invention

The present invention relates generally to slings, bandages, supports and swathes for the treatment of injuries to the upper extremity of the body. More particularly, the invention relates to such devices capable of, for example, cradling and substantially immobilizing a portion of the upper extremity of the human body, such as an arm.

2. Description of the Related Art

The art to which the invention relates includes a variety of slings, including boyscout slings and the like, as well as the elastic bandages useful for wrapping portions of the human body to prevent or treat injuries thereto.

A common drawback associated with conventional slings found in the related art is the discomfort associated with wearing such devices, the size limitations such as small, medium, large and extra-large, and the inability to use a single device for left and right applications.

The discomfort experienced by the wearer of such a device is most often related to the manner in which the sling strap overlies the shoulder and neck region of the wearer. Quite often such a strap is very narrow and causes pinching or gouging as weight is applied to the sling. In addition, another drawback is associated with the inability of such a sling to be constrained and essentially immobilize the arm or other appendage being treated by compressing it against the torso of the wearer's body.

One such device designed to remedy the above-referenced drawbacks is an armsling set forth in U.S. Pat. No. 4,716,895 granted to Marques, et al. on Jan. 5, 1988, which is incorporated by referenced as if fully set forth herein.

The Marques patent is directed to a sling for support of the arm, comprising an elongated cloth body having a relatively wide central region and a relatively narrow end region and further having an arm extending outwardly and adjacent to central region. The body is mounted on one shoulder and supports the opposite arm, without the need the for any separate arm containing pouch or pocket. Hook and loop fasteners are provided to secure the ends of the arm to each other and to secure the arm to the body. Until now, a sling-like swathe capable of cradling the upper extremity and capable of being wound around the torso of the wearer to substantially immobilize the arm against the torso has not been invented.

SUMMARY OF THE INVENTION

The present invention is directed to a sling-like swathe device. An embodiment to the present invention includes a length of flexible material, preferably a tricot-backed, brushed nylon laminate fitted with an appendage receiving loop or pocket, and hook and loop type fasteners.

Preferably, the length of material is approximately four inches wide and ninety-six inches long, but other sizes may be more suitable for different applications and such are contemplated within the scope of the present invention. The central body portion of the device is substantially symmetrical about a midline.

In the preferred embodiment the device has a front and a back. The front has hook and loop cloth or fabric capable of receiving the hook component of the cooperating hook and loop attachment structure. The hook component is typically associated with the end of the device opposite the looped end. The device may also have an optional supplemental hook and loop section.

It is contemplated that any number of hook and loop sections may be positioned preferably on the back of the invention so as to enable the device to be universally applied to the body shapes and sizes of a variety of individuals from children to large adults.

The hook structure of the preferred embodiment may be removably attached to the back side of the device, but is preferably heat welded thereto. In addition, the loop or pocket is preferably formed by heat welding a folded over loose free end of material to the remaining length material. Of course, alternate embodiments of the present invention allow the hook and loop material and the loop at one end of the device to be stitched in place in order to accomplish the same or similar effect as heat welding.

The invention is therefore directed to a universal swathe for carrying and immobilizing an appendage about the torso of a wearer. The preferred apparatus is comprised of a length of substantially flexible, preferably inelastic, moisture absorbing, material permitting ventilation and aeration.

The swathe has a central portion substantially symmetrical about a midline and having a first end, a second end, a front and a back. The preferred material for the swathe is a tricot-backed, brushed nylon laminate.

The front is configured with a component of a cooperating hook and loop structure. The end typically comprises a pocket or loop for receiving an appendage, and the second end has the other component of the cooperating hook and loop structure typically attached to the back of the flexible material.

The pocket is preferably formed by folding a portion of the length of flexible material over itself and securing it to the remaining length of flexible material. The swathe includes supplemental attachment structure in addition to the hook and loop attachment structure associated with the first end.

The loop component of the cooperating hook and loop material is preferably associated with the front of the swathe and the hook component of the cooperating hook and loop material is associated with the first end.

The pocket and the hook component are attached by an attachment structure selected from the group of attachment structures consisting of heat welding, gluing, hook and loop structure, fasteners, and stitching.

The invention is also directed to a method of immobilizing an appendage by using the inventive apparatus, comprising the following steps. The user inserts an appendage into the pocket, wraps the length of the material about the body to immobilize the appendage, and attaching the free end to the material via the cooperating hook and loop structure.

The preferred wrapping step includes wrapping the material diagonally across the back of the wearer, and wrapping the material horizontally around the torso of the wearer.

BRIEF DESCRIPTION OF THE DRAWINGS

With reference to FIGS. 1 through 4, an embodiment of the present invention is designated generally by the reference numeral 10. Embodiment 10 incorporates a length of flexible material, preferably a tricot-backed, brushed nylon laminate. It is contemplated that other suitable materials may be used, but the aforementioned material is preferred.

Figure 1:
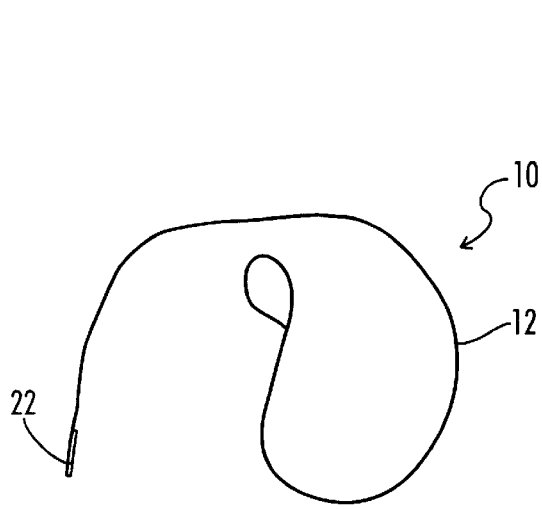
FIG. 1 is a side view of an embodiment of the present invention illustrating a looped end positioned opposite a free end.

The preferred material 12 typically has a front surface 14 and a back surface 16. The significance of the front and back surfaces will become apparent, but it should be understood that a material having two "front sides" as opposed to a front and a back can be used. Spaced apart ends 18 and 20 are configured differently. End 18 preferably has a component of hook and loop material 22 attached thereto. Preferably, the component is the hook structure of the aforementioned hook and loop material.

Figure 2:
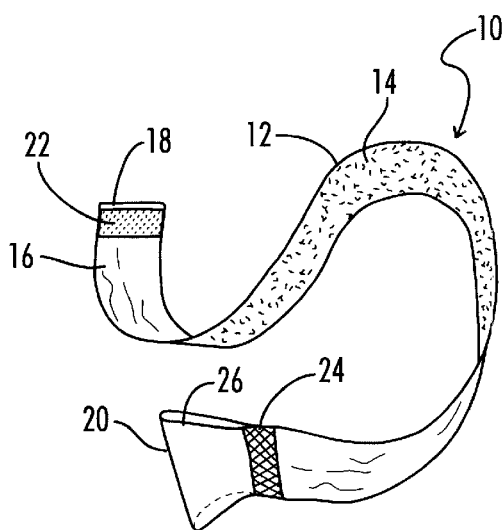
FIG. 2 is a perspective view of the embodiment shown in FIG. 1.
Figure 3:
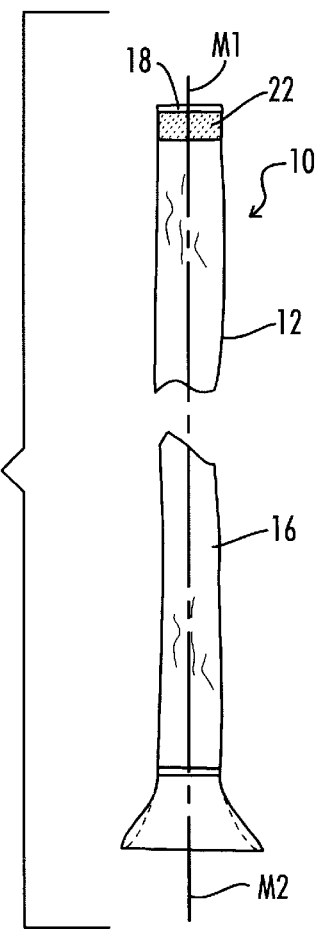
FIG. 3 is a rear perspective view of the embodiments of the invention shown in FIGS. 1 and 2.
Figure 4:
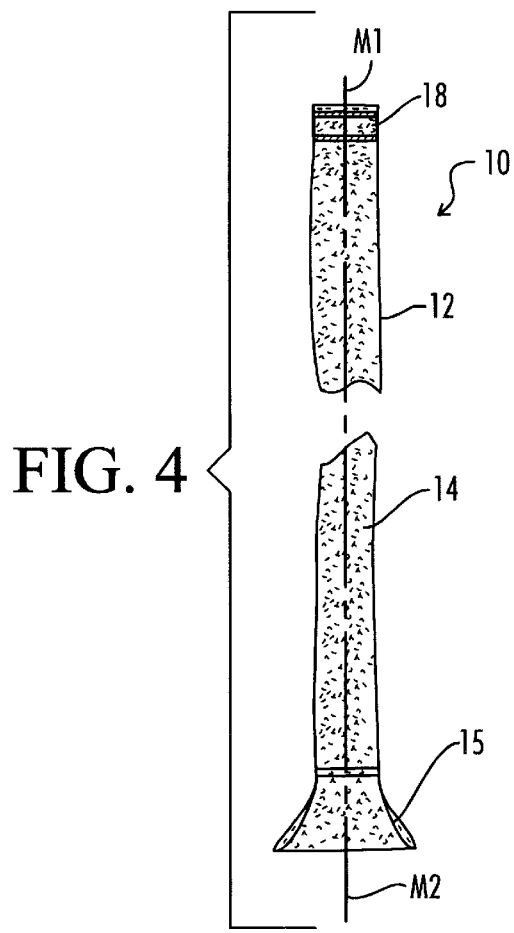
FIG. 4 is a front perspective view of the embodiments shown in FIGS. 1 through 3.

As illustrated in FIGS. 2 through 4, hook portion 22 is only visible from the back side 16 of the material 12. The hook material 22, or the loop material in alternate embodiments, is preferably heat welded to the length of material 12, but it may also be stitched, glued or even removably attached thereto.

Looped end 20 opposite free end 18 is preferably formed by folding over a length of the material 12 back onto itself and heat welding the combination indicated by reference numeral 24. Again, the heat weld can be replaced by stitching or gluing, or any other suitable means of attachment so long as the loop is positively attached to the length of material 12 when the user wears the invention. Accordingly, associated with the looped end 20 is a pocket 26 capable of receiving an appendage as illustrated in FIG. 5.

Figure 5:
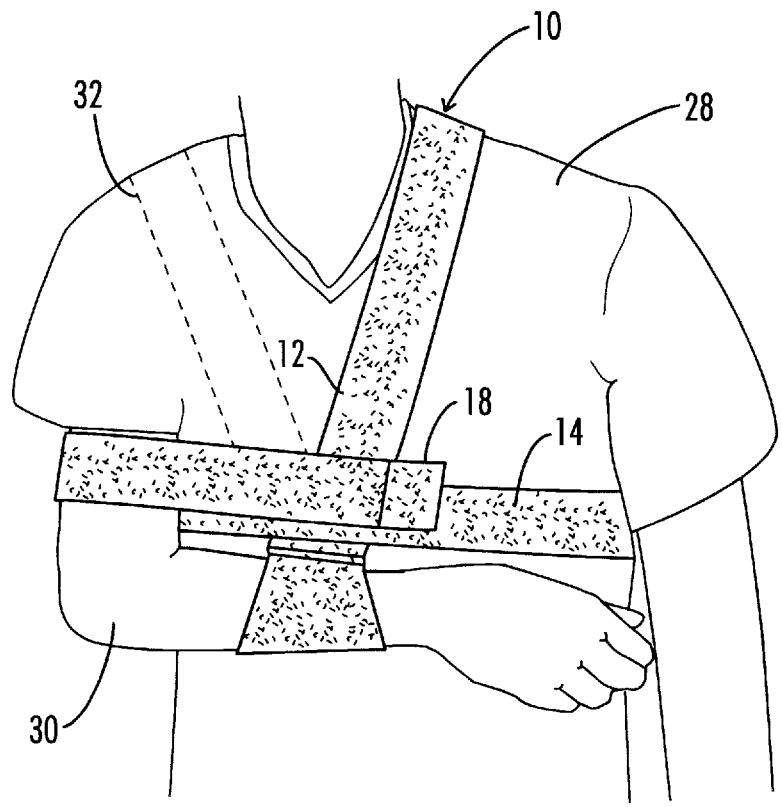
FIG. 5 is a perspective view of the embodiments shown in FIGS. 1 through 4 as applied to the torso of a human.
Figure 6:
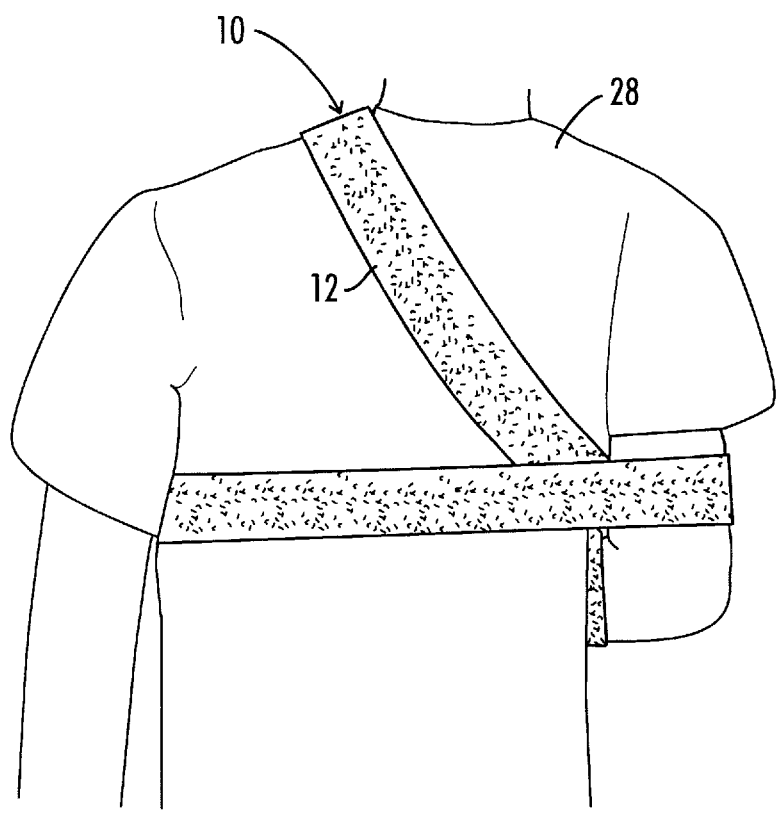
FIG. 6 is a rear perspective view of the invention shown in FIGS. 1 through 5 as applied to the torso of the body of the wearer shown in FIG. 5.

With reference to FIG. 5 the embodiment of the present invention designated generally by the reference numeral 10 is shown attached to the upper extremity of the wearer 28. Of course, the embodiment of the invention 10 can be wrapped in a variety of ways around the wearer 28 but is preferably wrapped as shown in FIGS. 5 and 6. Of course, the mirror image (not shown) of the wrap direction would be preferred with the wearer's left arm.

In use, the wearer 28 inserts an extremity such as an arm 30 into the pocket 26 (see FIG. 2). The remaining length 12 of the material is first draped over the shoulder opposite the arm positioned in the loop at a position adjacent the clavicle and neck region of the wearer 28. The embodiment of the invention 10 is then preferably wrapped and diagonally across the wearer's back (FIG. 6), and horizontally around the torso of the wearer to constrain the arm against the torso as shown.

The preferred length of the material enables the user to encircle the torso at least one time to accomplish the substantially constraining and immobilizing function of the invention. After the length 12 is wrapped horizontally around the torso, free end 18 having the preferred cooperating hook configuration described above with respect to FIG. 2, is pressed against the cooperating loop structure of the front 14 for engagement.

In this fashion, the appendage of the wearer is held in a sling-like fashion by the invention and substantially immobilized by the remaining length of material. With reference to FIG. 6, the preferred direction in which the invention is wrapped is illustrated as shown from the back side of the wearer.

Alternate embodiments of the present invention substantially incorporate the structure described above, but also contemplate the use of moisture absorbing material to collect and remove moisture from the skin of the wearer. Such embodiments are particularly useful during warm or balmy periods of the day in which the invention is worn. In addition, in the event the shoulder or clavicle region illustrated in FIGS. 5 and 6 onto which the length of material 12 is wrapped is sensitive or sore, the user simply repositions the material 12 as illustrated by the dashed lines of FIG. 5 and designated by the referenced numeral 32. In this fashion the wearer may choose to wrap the invention in the reverse horizontal direction to that shown in FIG. 5.

As illustrated and described, the preferred method of wrapping the invention about the torso of the human body incorporates a diagonal placement of a portion of the length of material 12 across the back of the wearer as illustrated generally in FIG. 6. Such diagonal wrapping enables the wearer to minimize slippage of the invention and therefore having to rewrap the invention if it has slipped. That is, the force transfer associated with a diagonal wrap as illustrated generally in FIGS. 5 and 6 provides the additional reliability needed for such a universal device.

The device is symmetrical about a midline, M1 and M2, as demonstrated by FIGS. 3 and 4. Such symmetry is particularly useful for wearing the invention as a universal left or right device.

These and other embodiments of the present invention will become apparent, and all are contemplated to be included within the scope of the invention whose only limitation is the construction of the appended claims.

What is claimed is:

1. A universal swathe for carrying and immobilizing an appendage about the torso of a wearer, comprising:

a length of substantially flexible material that is symmetrical about a midline and having a first end, a second end, a front and a back, wherein the front is comprised of a component of a cooperating hook and loop structure;

the first end comprising a pocket for receiving an appendage;

the second end having the other component of the cooperating hook and loop structure attached to the back of the flexible material; and the pocket is a continuous closed loop and the length of substantially flexible material is of a sufficient length, longer than the circumference of the wearer's torso, enabling it to be wrapped transversely about the torso of the wearer and overlie the appendage to immobilize it against the torso.

2. The swathe of claim 1 wherein the substantially flexible material is tricot-backed, brushed nylon laminate.

3. The swathe of claim 1 wherein the pocket is formed by folding a portion of the length of flexible material over itself and securing it to the remaining length of flexible material.

4. The swathe of claim 1 including supplemental attachment structure in addition to the hook and loop attachment structure associated with the first end.

5. The swathe brushed, of claim 1 wherein the loop component of the cooperating hook and loop material is associated with the front of the swathe and the hook component of the cooperating hook and loop material is associated with the first end.

6. The swathe of claim 5 wherein the pocket and the hook component are attached by an attachment structure selected from the group of attachment structures consisting of heat welding, gluing, hook and loop structure, fasteners, and stitching.

7. The swathe of claim 1 wherein the length of substantially flexible material is substantially inelastic.

8. The swathe of claim 1 wherein the length of substantially flexible material is moisture absorbent.

9. The swathe of claim 1 wherein the length of substantially flexible material permits ventilation and aeration.

10. A universal human appendage immobilizing device, comprising:
    a swathe formed from a length of flexible material that is symmetrical about a mid-line, wherein the swathe includes a central body portion, a first end, a second looped end, a back, and a front;
    cooperating hook and loop attachment structure, wherein the first end has the hook structure and the front has the loop structure of the cooperating hook and loop attachment structure; and
    the looped end extending from and merging with the central body portion, and the hook structure are attached by an attachment structure selected from the group of attachment structures consisting of heat welding, hook and loop structure, gluing, fasteners, and stitching, the length of flexible material is of a sufficient size, longer than the circumference of a wearers torso, enabling it to be wrapped transversely about the torso of the wearer to immobilize the appendage against the torso.

11. The swathe of claim 10 wherein the flexible material is tricot-backed, brushed, nylon laminate.

12. The swathe of claim 10 wherein the looped end is formed by folding a portion of the length of flexible material over itself and securing it to the remaining length of flexible material.

13. The swathe of claim 10 including supplemental attachment structure in addition to the hook and loop attachment structure associated with the first end.

14. The swathe of claim 10 wherein the central body portion is substantially symmetrical about a midline.

15. The swathe of claim 10 wherein the length of substantially flexible material is substantially inelastic.

16. The swathe of claim 10 wherein the length of substantially flexible material is moisture absorbent.

17. The swathe of claim 10 wherein the length of substantially flexible material permits ventilation and aeration.

18. A method of immobilizing an appendage of a wearer about the wearer's body, comprising the steps of:
    providing a length of substantially flexible material that is symmetrical about a mid-line with a closed looped first end extending from and merging with the length of substantially flexible material, a free second end, a front and a back, wherein the front is configured with a component of a cooperating hook and loop structure;
    inserting an appendage into the closed looped first end;
    wrapping the length of the material about the body of a wearer to encircle the body and pin the appendage against the body to immobilize the appendage; and
    attaching the free second end to the material via the cooperating hook and loop structure.

19. The method of claim 18 wherein the step of wrapping includes wrapping the material diagonally across the back of the wearer.

20. The method of claim 18 wherein the step of wrapping includes wrapping the material horizontally around the torso of the wearer.

* * * * *